(12) United States Patent
Hamilton et al.

(10) Patent No.: US 7,066,175 B2
(45) Date of Patent: Jun. 27, 2006

(54) PORTABLE GAS POWERED POSITIVE PRESSURE BREATHING APPARATUS AND METHOD

(75) Inventors: Robert M. Hamilton, Brea, CA (US); Anthony J. Gambone, Laguna Niguel, CA (US)

(73) Assignee: Emergent Respiratory Products, Inc., Irvine, CA (US)

( * ) Notice: Subject to any disclaimer, the term of this patent is extended or adjusted under 35 U.S.C. 154(b) by 425 days.

(21) Appl. No.: 10/020,544

(22) Filed: Nov. 29, 2001

(65) Prior Publication Data

US 2002/0162553 A1 Nov. 7, 2002

Related U.S. Application Data

(60) Provisional application No. 60/288,713, filed on May 7, 2001.

(51) Int. Cl.
*A62B 9/02* (2006.01)
*A61M 16/00* (2006.01)

(52) U.S. Cl. .............................. 128/205.24; 128/204.23

(58) Field of Classification Search ........... 128/204.21, 128/205.24, 204.18, 204.23, 204.24, 204.25, 128/204.26, 205.11
See application file for complete search history.

(56) References Cited

U.S. PATENT DOCUMENTS

| | | | |
|---|---|---|---|
| 2,608,200 A * | 8/1952 | Stockman ................. 137/81.1 |
| 2,608,971 A * | 9/1952 | Holmes ..................... 137/81.1 |
| 2,988,085 A | 6/1961 | Jones | |
| 3,362,404 A | 1/1968 | Beasley | |
| 3,752,175 A | 8/1973 | Hamilton et al. | |
| 3,795,257 A | 3/1974 | Fabish et al. | |
| 3,834,383 A * | 9/1974 | Weigl et al. ........... 128/204.26 |
| 3,859,995 A | 1/1975 | Colston | |
| 3,952,773 A * | 4/1976 | Hahn ......................... 137/114 |
| 4,141,356 A * | 2/1979 | Smargiassi ............. 128/204.23 |
| 4,278,110 A * | 7/1981 | Price et al. .................. 137/805 |
| 4,655,213 A | 4/1987 | Rapoport et al. | |
| 4,667,670 A | 5/1987 | Feathers | |
| 4,773,411 A | 9/1988 | Downs | |
| 4,821,767 A | 4/1989 | Jackson | |
| 4,838,257 A * | 6/1989 | Hatch ..................... 128/204.18 |
| 4,877,023 A * | 10/1989 | Zalkin ..................... 128/204.21 |
| 4,971,050 A * | 11/1990 | Bartos ..................... 128/204.18 |
| 5,000,174 A | 3/1991 | Gray et al. | |
| 5,040,529 A * | 8/1991 | Zalkin ..................... 128/204.18 |
| 5,074,298 A * | 12/1991 | Arnoth ..................... 128/204.18 |
| 5,148,802 A | 9/1992 | Sanders et al. | |

(Continued)

Primary Examiner—Teena Mitchell
(74) Attorney, Agent, or Firm—Knobbe, Marten, Olson & Bear LLP

(57) ABSTRACT

A portable positive pressure breathing apparatus includes a demand valve with a supply inlet port adapted to be connected to a pressurized source of oxygen and an outlet port adapted to be connected to the inlet of a patient's breathing appliance. The demand valve further includes a reference chamber and a valve assembly responsive to the reference chamber/appliance inlet pressure differential for connecting/disconnecting the inlet port to and from the outlet port. At least one manually adjustable back pressure regulator is connected to the pressure source and the reference chamber for setting the pressure in the reference chamber (and inlet to the breathing appliance) at a selected level above atmospheric pressure.

17 Claims, 14 Drawing Sheets

U.S. PATENT DOCUMENTS

| | | | |
|---|---|---|---|
| 5,237,987 A * | 8/1993 | Anderson et al. ...... | 128/204.18 |
| 5,245,997 A | 9/1993 | Bartos | |
| 5,357,950 A | 10/1994 | Wippler et al. | |
| 5,360,000 A * | 11/1994 | Carter .................... | 128/204.26 |
| 5,433,193 A | 7/1995 | Sanders et al. | |
| 5,460,175 A * | 10/1995 | Foote et al. ........... | 128/205.24 |
| 5,464,009 A | 11/1995 | Tatarek-Gintowt | |
| 5,632,269 A | 5/1997 | Zdrojkowski | |
| 5,666,945 A * | 9/1997 | Davenport ............. | 128/200.14 |
| 5,685,296 A | 11/1997 | Zdrojkowski et al. | |
| 5,787,882 A | 8/1998 | Hamilton | |
| 6,116,242 A * | 9/2000 | Frye et al. .............. | 128/205.24 |
| 6,237,594 B1 * | 5/2001 | Davenport ............. | 128/204.26 |
| 6,318,366 B1 * | 11/2001 | Davenport ............. | 128/205.24 |
| 6,378,520 B1 * | 4/2002 | Davenport ............. | 128/204.26 |
| 6,571,796 B1 * | 6/2003 | Banner et al. ......... | 128/204.26 |

* cited by examiner

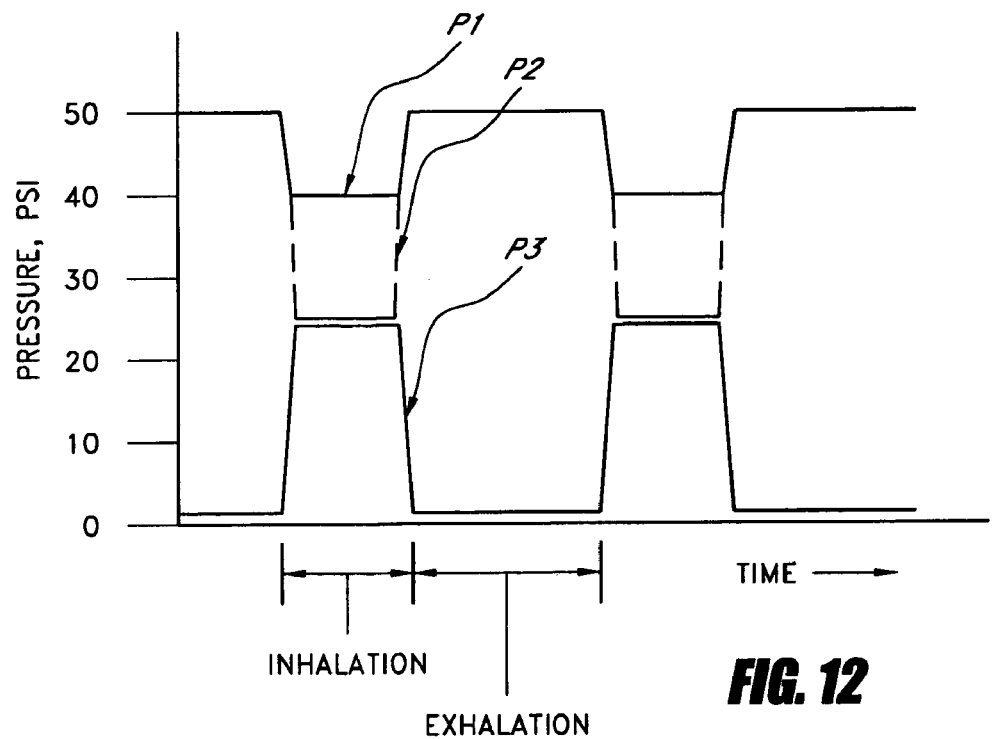
FIG. 12
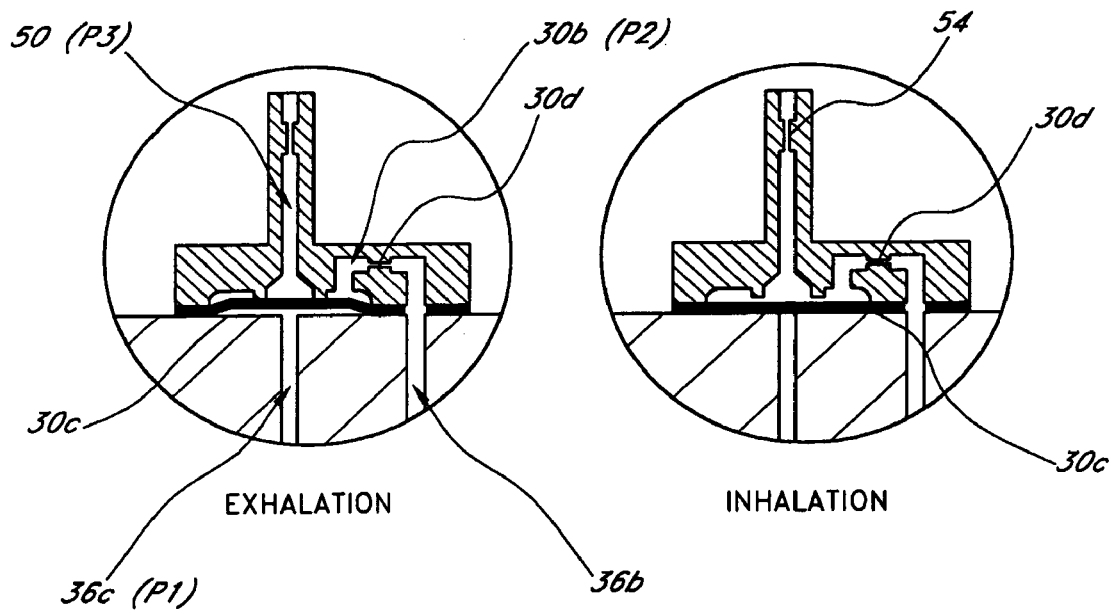
FIG. 10  FIG. 11

PORTABLE GAS POWERED POSITIVE PRESSURE BREATHING APPARATUS AND METHOD

RELATED APPLICATION

This application is a continuation-in-part of provisional application no. 60/288,713, filed May 7, 2001.

FIELD OF THE INVENTION

The present invention relates to an apparatus and method for use in respiratory therapy and more particularly to a portable system for use in supplying a continuous and/or dual level positive airway pressure treatment to a patient in respiratory distress and method. As used herein the term oxygen or $O_2$ includes air and oxygen enriched air as well as purified $O_2$.

BACKGROUND OF THE INVENTION

Individual's suffering from pulmonary edema, i.e., the effusion of serous fluid into the lungs, and certain other respiratory ailments are generally treated by forcing breathable gas, normally oxygen ($O_2$) into the lungs and maintaining the pressure within the lungs at a level, e.g., 1 to 20 centimeters of water above atmospheric. The $O_2$ can be supplied directly to the lungs through an endotracheal tube, one end of which is inserted into the lungs through the individual's mouth, i.e., intubation. The invasive technique of intubation requires considerable skill and can cause serious injury to the patient. Also, the recovery time of intubated patients may be considerable.

Alternatively, a patient may be fitted with a breathing appliance such as a face mask which is equipped with an inlet for receiving oxygen under pressure and an inhalation/exhalation valve for exhausting exhaled air to the atmosphere. The respiratory departments of many hospitals have relatively sophisticated equipment for supplying oxygen at continuous and/or dual level pressure to such appliances. However, such equipment is neither readily portable nor simple to operate and often is not available in emergency rooms.

Portable systems are currently available for use in emergency rooms by nurses and in the field by emergency rescue personnel, e.g., paramedics, for the continuous positive airway pressure ("CPAP") procedure. However, such portable systems conventionally rely on a spring loaded check valve located in or near the face mask to set the maximum pressure in the mask. The check valve serves to bypass the oxygen stream to the atmosphere during the patient's exhalation phase. The flow rate is normally adjusted to accommodate a patient's peak inhalation flow rate, e.g., 75 to 100 liters per minute (l/m). A patient typically inhales around 10 to 12 l/m with each exhalation phase exceeding the time duration of the inhalation phase by a factor of two or more.

As a result, currently available portable systems for use by emergency rescue personnel consume oxygen at a high rate stemming from the fact that they are continuous flow devices that must cater to high demand and waste $O_2$ during the longer expiration phase of the respiratory cycle. Also, this high flow rate creates unwanted additional expiratory work for the patient.

In a normal respiratory cycle the torso muscles act to expand the lungs and thus draw air into them during the inhalation cycle. Exhalation is accomplished by the muscles relaxing and the elastic recoil of the chest forcing air from the lungs. During positive pressure breathing the muscle action is reversed so that air enters the lungs under pressure and exhalation requires forceful action by the abdominal muscles. Thus, exhalation under conventional CPAP treatment involves a significant amount of exertion for the patient.

The shock to a patient being suddenly confronted with a significant amount of pressure in his or her airway, e.g., 10 to 20 cm $H_2O$ during inhalation/exhalation is another disadvantage of the currently available portable CPAP systems.

U.S. Pat. No. 5,148,802 and related U.S. Pat. Nos. 5,433,193 and 5,632,269, while not directed to portable CPAP systems for use by emergency rescue personnel, disclose a sophisticated system ("'802 system") employing the CPAP treatment for individuals suffering from sleep apnea. The '802 system, which is designed to keep the individual's airway continuously open during sleep, employs a sensitive flow sensor and complicated electronic circuitry to determine when the user is exhaling and lowers the applied pressure during the expiratory phase.

The '802 system is expensive and, as with many complicated electronic devices, would be subject to failure if mishandled.

There is a need for a simple, inexpensive, reliable, portable and rugged apparatus which can be used by emergency rescue personnel whether in the field or in emergency rooms to ventilate a patient's lungs with oxygen under continuous positive airway pressure.

SUMMARY OF THE INVENTION

A continuous positive airway pressure apparatus or system for supplying $O_2$ from a pressurized source to an individual's breathing appliance in accordance with the present invention includes a demand pressure regulator for supplying $O_2$ to the patient's breathing appliance, e.g., a face mask, only when demanded. The system includes a demand valve with a supply inlet port adapted to be connected to the pressurized source, an outlet port adapted to be connected to the appliance's inlet, a reference chamber and a valve assembly responsive to the reference chamber/appliance inlet pressure differential for connecting and disconnecting the inlet port to and from the outlet port.

The system further includes at least one manually adjustable back pressure regulator connected to the pressurized source and the reference chamber for setting the pressure in the reference chamber (and inlet to the breathing appliance) at a selected level above atmospheric pressure.

Optionally the system may include an additional manually adjustable or fixed back pressure regulator with one regulator controlling the back pressure during inhalation and the other controlling the back pressure during exhalation and connected to the reference chamber to act in parallel or series to create bi-level pressures. The system may also include a nebulizer outlet for supplying low flow $O_2$ to a nebulizer during the patient's inhalation phase. In addition, a preferred patient valve to be attached to or incorporated in the breathing appliance may be used with the adjustable back pressure regulator/demand valve. The improved patient valve maintains the pressure in the patient's airway very close to the selected back pressure during inhalation and exhalation regardless of the magnitude of the selected pressure level. The improved patient valve is particularly advantageous where the reference back pressure remains the same during the entire breathing cycle.

A method of treating a patient suffering from pulmonary edema or other respiratory ailment in accordance with the present invention includes the following steps:

a) securing a breathing appliance to the patient's airway with the appliance having an inlet and an inhalation/exhalation valve to allow breathable gas passing through the inlet to enter the patient's lungs during the inhalation phase and allow expired air to exit to atmosphere during the exhalation phase;

b) providing a pressurized source of $O_2$;

c) providing at least one reference pressure at a selected value above atmospheric pressure;

d) monitoring the pressure at the appliance inlet;

e) comparing the appliance inlet pressure with the reference pressure;

f) connecting and disconnecting the pressurized source to the mask inlet when the inlet pressure falls below and rises to the reference pressure, respectively; and g) varying the selected value of the reference pressure during the treatment.

The construction and operation of the present invention may best be understood by reference to the following description taken in conjunction with the appended drawings, wherein like components are designated with the same reference numeral in the several figures.

BRIEF DESCRIPTION OF THE DRAWINGS

FIGS. 10 and 11 are cross-sectional schematic views of the nebulizer valve configured in the exhalation and inhalation modes, respectively;

FIG. 12 is a pressure diagram showing pressures at several points in the system relevant to the operation of the nebulizer valve;

DESCRIPTION OF THE PREFERRED EMBODIMENT

Figure 1:
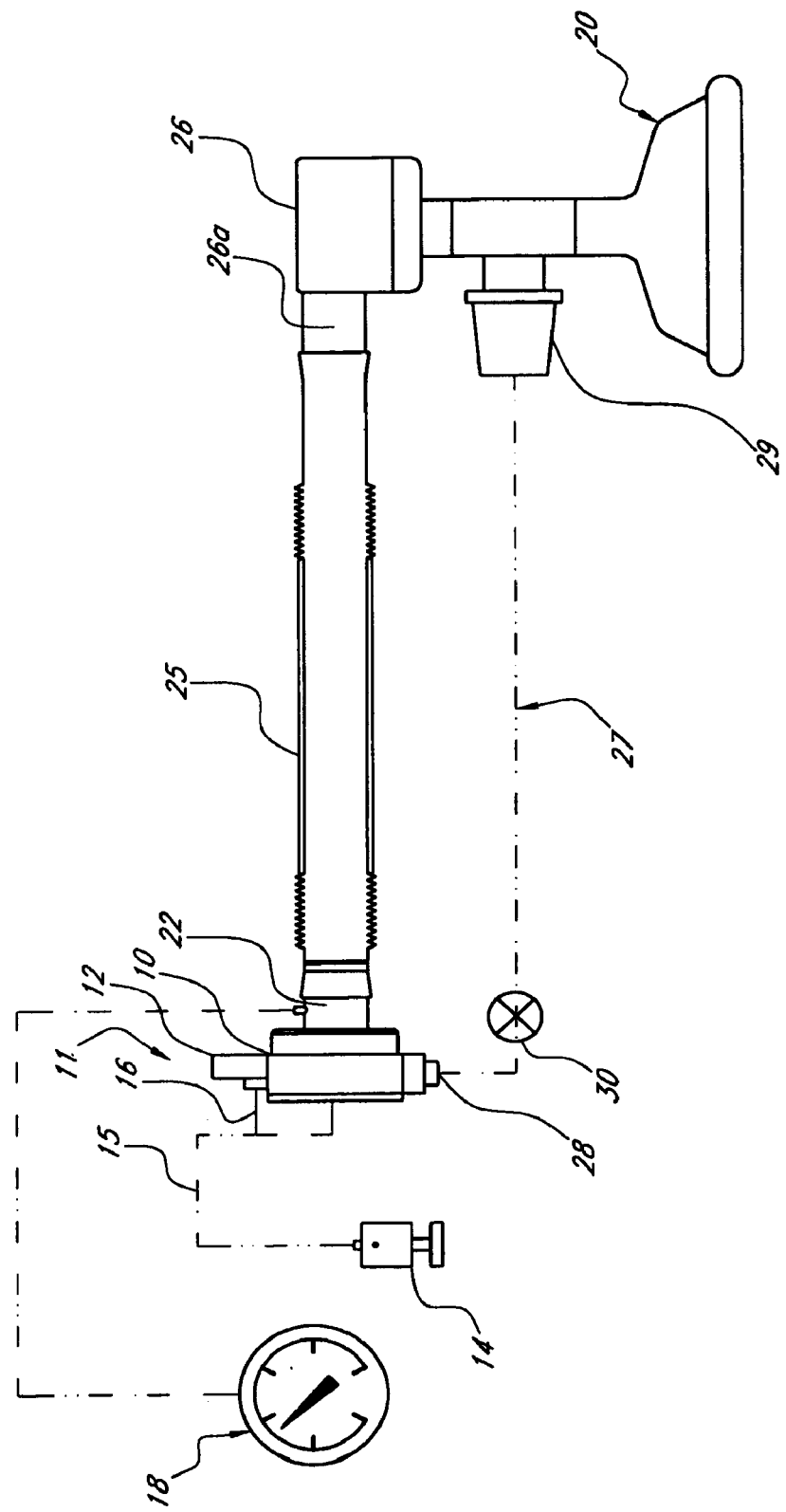
FIG. 1 is a system schematic of the present invention in an assembled state with a face mask and nebulizer.

Referring now to the drawings, and particularly to the system schematic of the invention shown in FIG. 1, a demand oxygen regulator 10 is powered by a pressurized $O_2$ source 11 through an inlet port 12. An adjustable back pressure regulator 14 receives pressurized $O_2$ on conduit or line 15 through a flow restrictor 16. A pressure gauge 18 provides a measure of the pressure within the outlet 22 of a demand oxygen regulator 10. $O_2$, at the desired pressure, is supplied from the demand oxygen regulator outlet 22, to a mask 20, via an inlet 58a of a balanced inhalation/exhalation patient valve 58 attached to or incorporated into the mask, and a conventional hose or tube 25. The inlet 58a is hereinafter sometimes referred to as the breathing appliance inlet.

Low flow $O_2$ is also supplied to a nebulizer 26 from a nebulizer outlet 28, and a nebulizer shut off valve 30 (incorporated in the pressure regulator as will be described in more detail) and line 27. The output of the nebulizer is combined with the $O_2$ delivered to the patient's mask through the tube 25 29 in a conventional manner.

Figure 2:
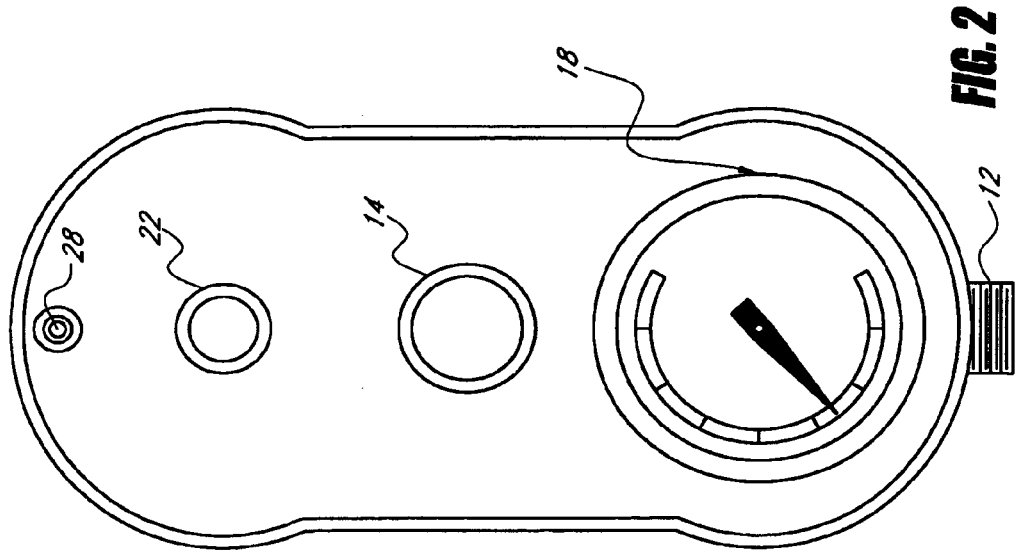
FIG. 2 is a front view of a housing in which the various components of the invention are mounted.
Figure 3:
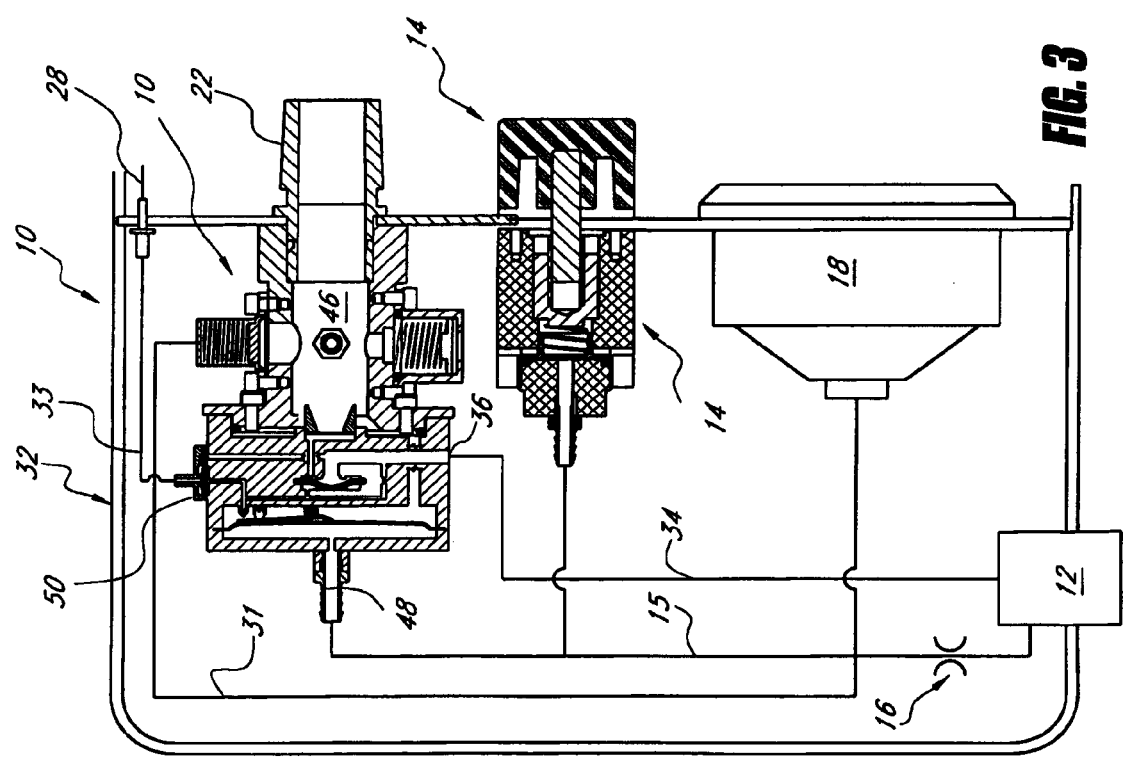
FIG. 3 is a cross-sectional view of the components demand valve within the housing including a pressure regulator, pressure gauge, a maximum pressure relief valve and an anti-suffocation relief valve.

Referring now to FIGS. 2 and 3 the demand oxygen regulator 10, back pressure regulator 14 and pressure gauge 18 are mounted within a housing 32. The pressure gauge 18 is placed in fluid communication with the outlet 22 via line 31. Line 33 connects the outlet of a nebulizer valve (to be described) to the outlet 28. Line 34 connects a supply inlet 36 of the demand regulator 10 to the $O_2$ inlet nipple 12.

Figure 4:
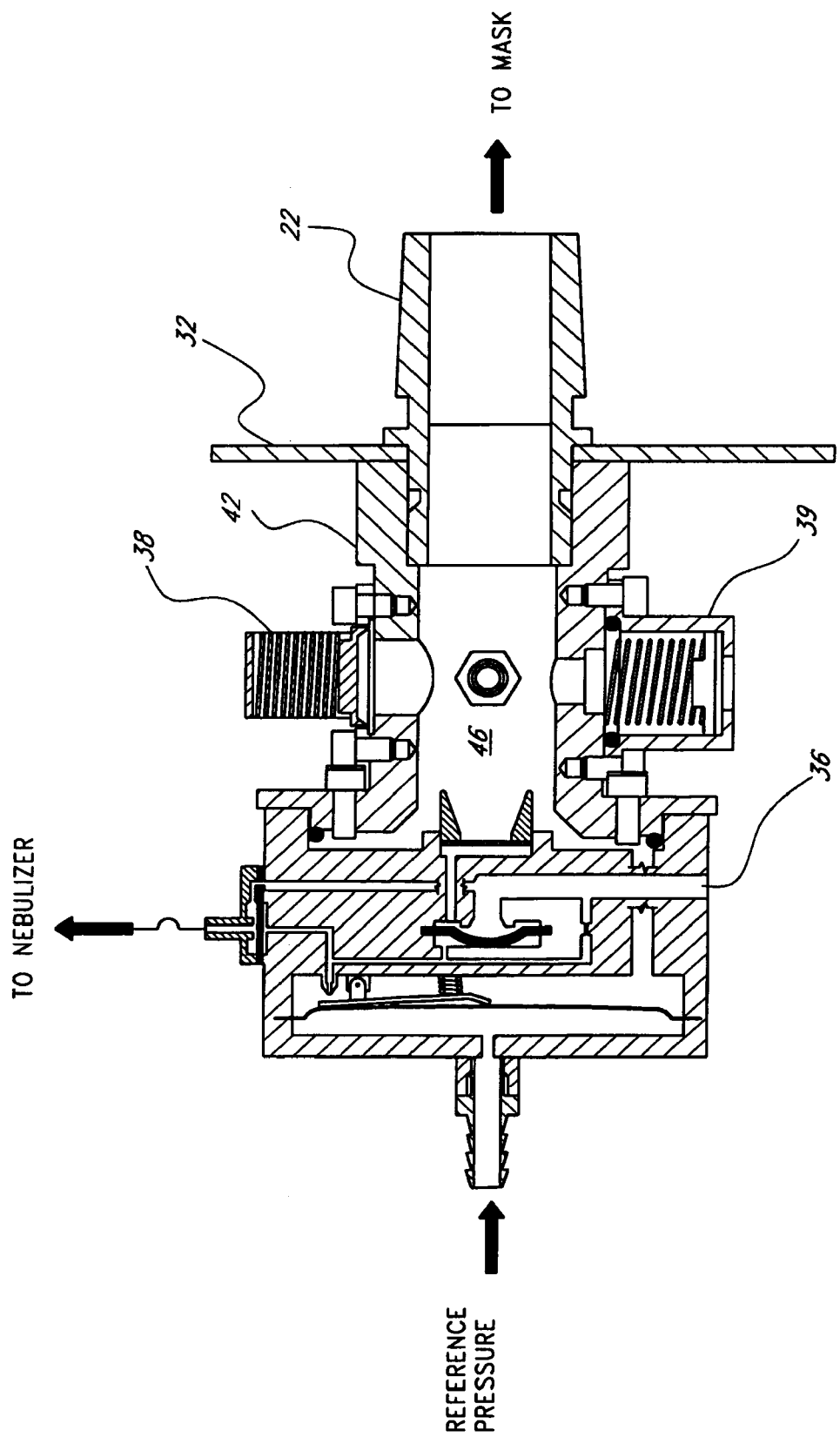
FIG. 4 is a cross-sectional view of the demand valve and the two relief valves.

Referring now to FIG. 4 the demand $O_2$ regulator 10 includes a demand valve 40, a maximum pressure relief valve 38 and an anti-suffocation valve 39. The valves 38 and 39 are mounted in a housing 42 which is secured to the demand valve housing by bolts, for example. The upstream interior section of the housing 41 42 forms the outlet port 46 for the demand valve, as will be discussed in more detail in connection with FIGS. 7 and 8.

The relief and anti-suffocation valves are conventional poppet valves with the valves 38 and 39 opening when the pressure in demand valve outlet 46 reaches a preset maximum value or falls below atmospheric pressure, respectively. The demand valve 40 includes the supply inlet 36, the outlet port 46, a reference pressure inlet 48 and a nebulizer valve outlet 50. The internal components of the demand valve 40 will be described in conjunction with FIGS. 7 and 8.

Figure 5:
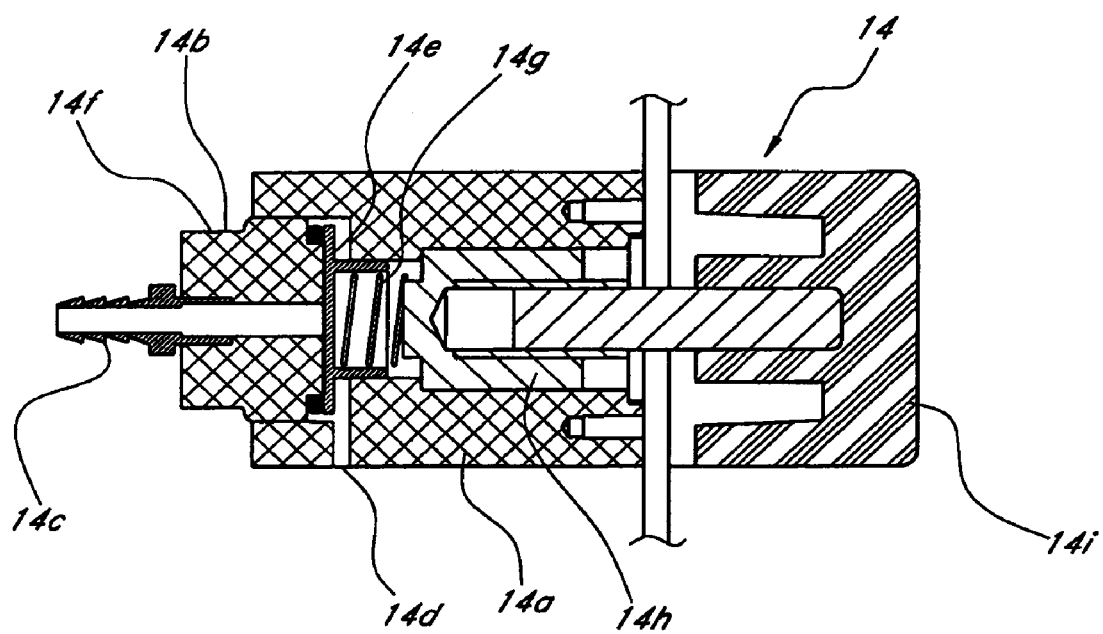
FIG. 5 is a cross-sectional view of the pressure regulator.

Referring now to FIG. 5 the back pressure regulator valve 14 is a conventional poppet valve with a top housing section 14a, a lower housing section 14b, an inlet 14c connected to the pressurized source via restrictor 16 (FIG. 3), an atmospheric outlet port 14d, and a valve plate 14e which is biased against seat 14f by spring 14g. An axially moveable plunger 14h responds to the rotation of knob 14i to adjust the compressive force applied by the spring to the valve plate 14e which in turn restricts the flow in line 15 from the $O_2$ source 11 to adjust the back pressure at inlet 14c, e.g., 1 to 20 cm $H_2O$ to establish the desired reference pressure in line 15a 15 to the demand valve as will be described in connection with FIGS. 7 and 8.

Figure 6:
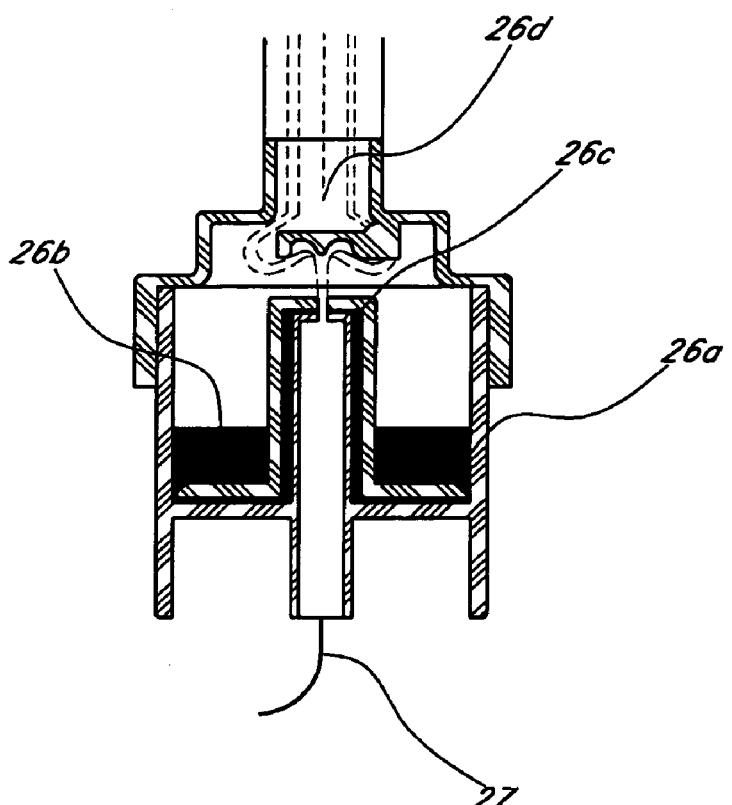
FIG. 6 is a schematic cross-sectional view of a nebulizer which may be used with the invention.

The nebulizer 26, as shown in FIG. 6, includes a container 26a for liquid medication 26b. Pressurized $O_2$ leaving nozzle 26c educts vaporized medication into stream 26d which enters the tube 29 adjacent the face mask during the inhalation phase of the patient's breathing cycle.

Figure 7:
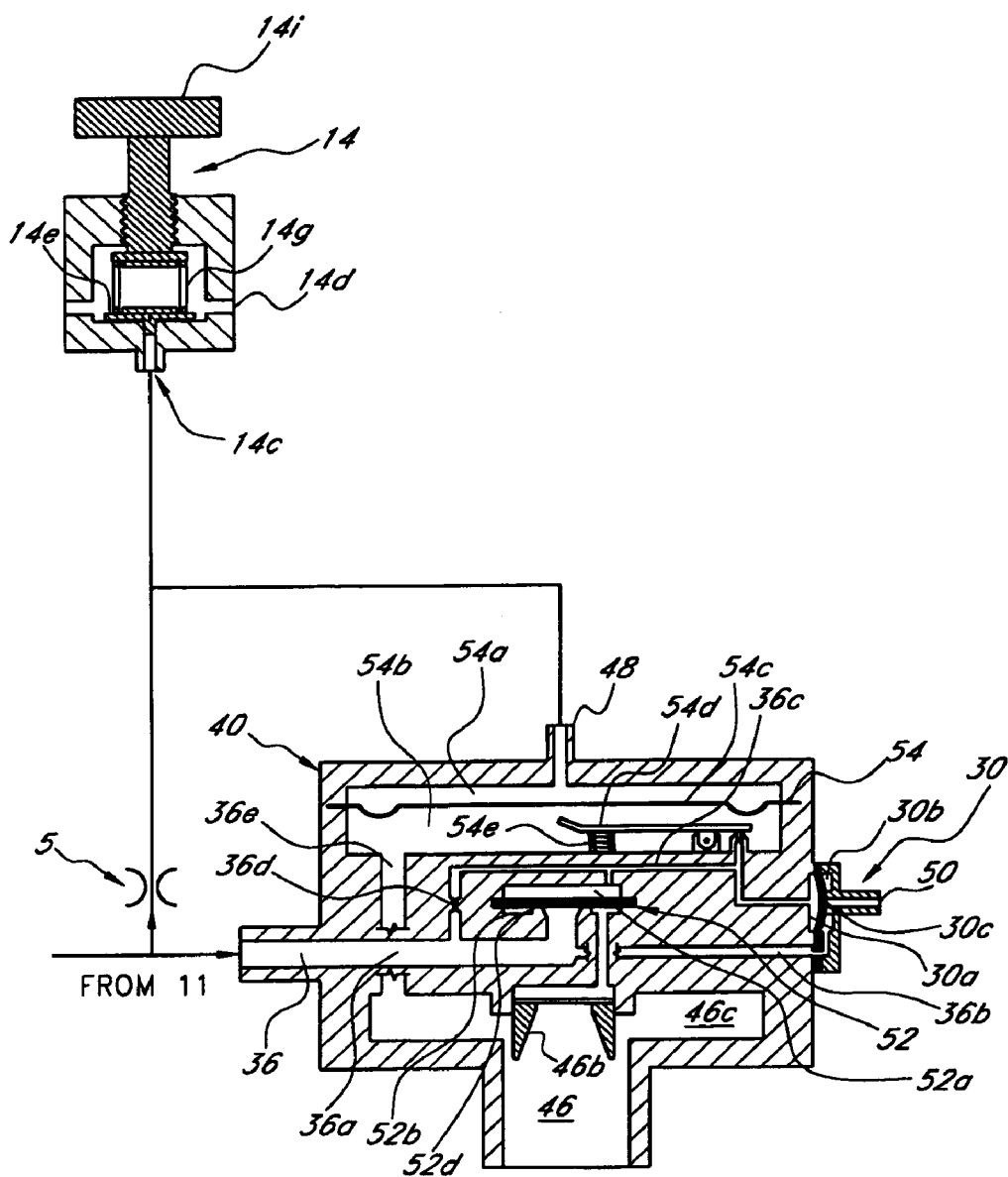
FIG. 7 is a cross-sectional schematic view of the demand valve and pressure regulator showing the demand valve as configured during a patient's exhalation phase.
Figure 8:
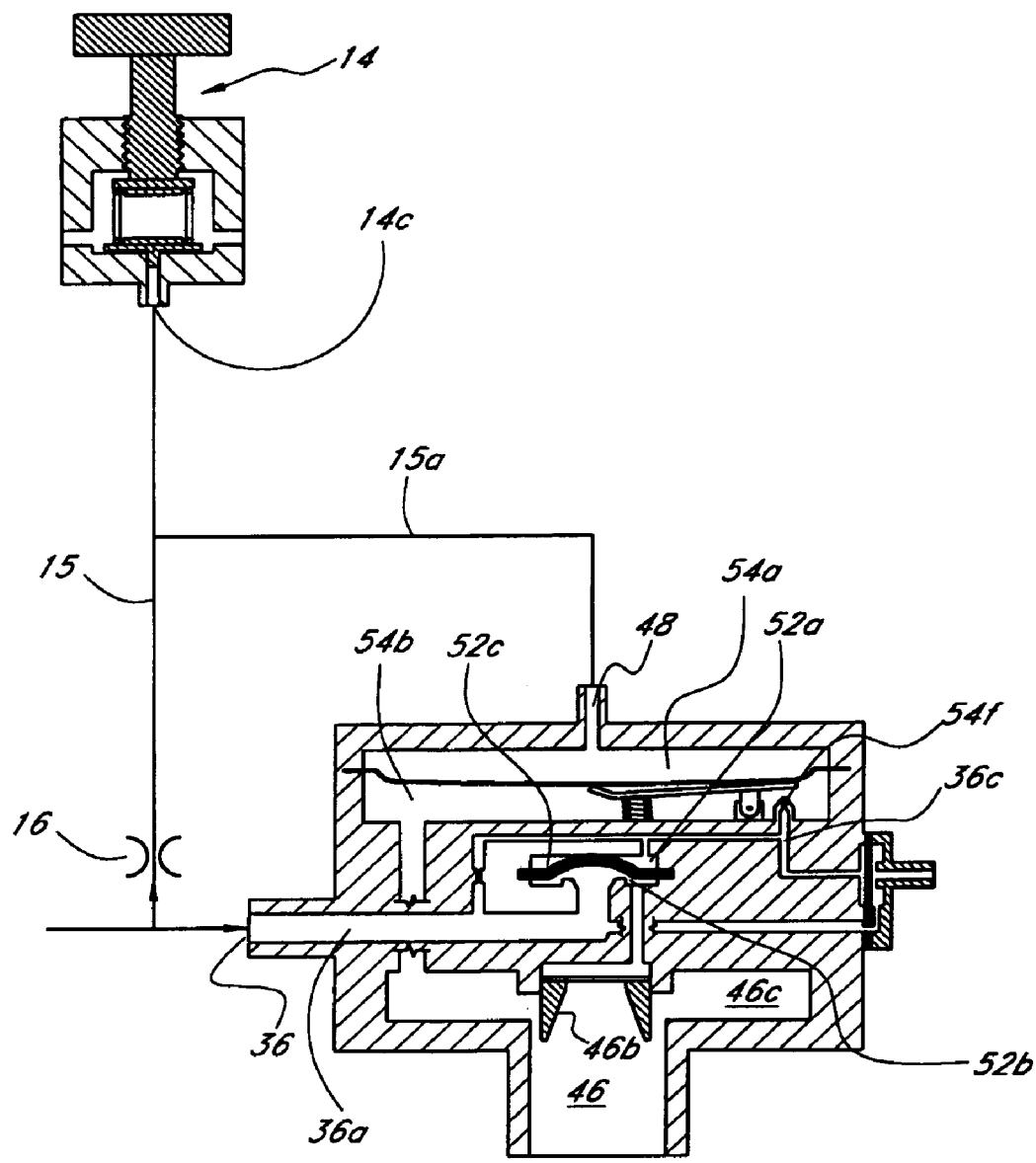
FIG. 8 is a cross-sectional schematic view of the demand valve and pressure regulator as configured during the inhalation phase.

Referring now to FIGS. 7 and 8 the demand valve 40 includes a main or first diaphragm valve 52 in which first and second chambers 52a and 52b are disposed on opposite sides of a moveable diaphragm 52c. The diaphragm 52c closes against a seat 52d disconnecting pressurized passage 36a and the inlet 30 from passage 46a when the pressures in chambers 52a and 52b are equal due to the greater exposed surface area on the top versus the bottom side of the diaphragm. A second diaphragm valve 54, which controls the operation of the main valve, has a pressure reference chamber 54a (open to the reference pressure inlet 48) and a second chamber 54b disposed on opposite sides of a sensing diaphragm 54c. The second valve also includes a normally closed spring biased paddle assembly comprising a pivotal arm 54d biased by spring 54e to normally close pilot valve orifice 54f.

The nebulizer (third) valve 30 includes chambers 30a and 30b, disposed on opposite sides of diaphragm 30c. The diaphragm 30c serves to close the nebulizer valve outlet 50 when the pressure in chambers 30a and 30b are equal due to the area of the diaphragm exposed to chamber 30b being greater than the area exposed to chamber 30a. A passageway 36b connects the chamber 30a to the inlet 36 as illustrated.

A passageway 36c connects the upper chamber 52a, the pilot valve orifice 54f and inner chamber 30a to the pressurized source via a flow restrictor 36d. Passageway 36e connects the lower chamber 54b of valve 54 to an outlet chamber 46c of the demand valve, which chamber extends above the outlet port and circumferentially around a nozzle 46b.

In the operation of the system of FIGS. 7 and 8 the pressure regulator 14, having been preset to the desired positive mask pressure, provides that reference pressure e.g., 1 to 20 cm $H_2O$ via line 15a to the reference chamber 54a. In the exhalation mode the main valve 52 is closed disconnecting the passage 46a and nozzle 46b from the inlet. When the patient begins to inhale the low pressure in the mask inlet, demand valve outlet port 46 and outlet chamber 46c falls slightly below the reference pressure in chamber 54a, and as a result, the diaphragm 54c moves downwardly to engage the paddle valve assembly arm 54d, and lift it off of the pilot valve seat 54f. This bleeds the high pressure $O_2$ in line 36c to the lower pressure chamber 54b and the outlet port.

The flow restrictor 36d allows the pressure in chamber 52a to drop below the pressure in inlet passage 36a a sufficient amount to cause the main valve 52 to open as is illustrated in FIG. 8, to initiate the inhalation mode. The main valve will remain open as long as the pressure in the mask inlet and outlet chamber 46c remains below the reference pressure. When the patient initiates his or her exhalation phase the pressure in the outlet port 46 and chamber 54b will rise to the reference pressure thereby releasing the diaphragm 54c from the paddle wheel arm 54d and allowing the spring to close the pilot valve 54f. This action immediately allows the pressure in the line 36c and chambers 52a to rise to a level sufficient to close the main valve as is shown in FIG. 7.

In this manner $O_2$ is supplied to the patient only on demand and at a pressure level which can be determined by the operator prior to and/or during the treatment. This results in a considerable saving of $O_2$ over the $O_2$ consumed by the conventional portable CPAP systems.

Figure 9:
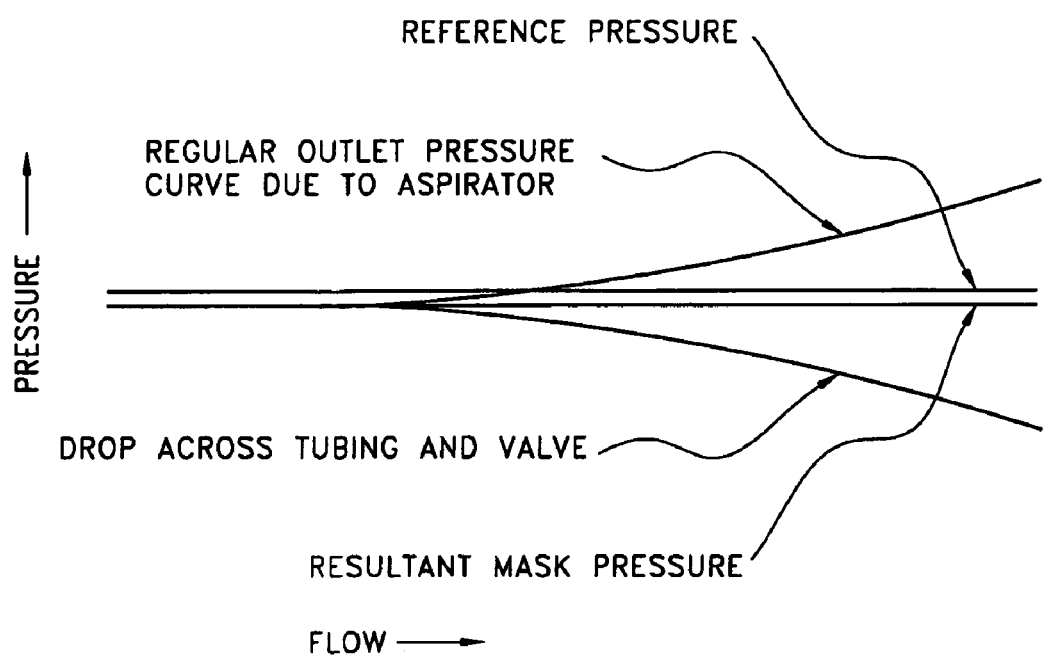
FIG. 9 is a pressure diagram illustrating how the pressure at various points in the system changes with the flow rate.

There is a pressure drop across the hose or tubing which connects the mask inlet to the demand valve outlet port as well as in the mask valve itself, which pressure drop is proportional to the $O_2$ flow rate. The demand valve outlet chamber 46c and nozzle 46b compensate for this loss as is illustrated in FIG. 9. The pressure in outlet chamber 46c is decreased by flow through the nozzle 46b, i.e., aspiration effect, in proportion to the flow rate. The nozzle and outlet chamber are designed, as illustrated in FIG. 9, to cause an increase in the pressure in the demand valve outlet port 46 (and decrease the pressure in the chamber 46c) which pressure increase mirrors the pressure drop across the tubing and mask valve as a function of flow rate. In this manner the resulting mask pressure is maintained almost equal to the adjusted reference pressure regardless of flow rate.

It is to be noted that the term pressure representative of the breathing appliance inlet pressure includes the pressure in the mask inlet and may include the demand valve outlet port pressure where the pressure loss in the tubing and/or patient valve is not compensated for.

The operation of the nebulizer valve 30 may best be understood by reference to FIGS. 10–12. The inlet pressure, e.g., 50 psi, is applied to both chambers 30a and 30b of the third valve 30 in the static condition, i.e., pilot valve 54f and main valve 52 are closed. In the absence of $O_2$ flow through the main valve 52, e.g., exhalation mode, the diaphragm 30c closes the nebulizer outlet 50 due to the unequal areas of the diaphragm exposed to the opposing chambers. When the pilot and main valves open, at the initiation of inhalation, the pressure (P1) in passageway 36c decreases immediately, as explained earlier, allowing the diaphragm 30c to open the nebulizer valve. This allows $O_2$ to flow through restrictor 30d (FIG. 10), into the nebulizer outlet 50, through restrictor 54 to the nebulizer nozzle 26c.

FIG. 12 is a pressure diagram showing the pressure at various points associated with the nebulizer during inhalation and exhalation. Curves P1, P2 and P3 represent the pressure in line 36b, chambers 30b and outlet 50, respectively during the inhalation and exhalation modes as indicated.

Figure 13:
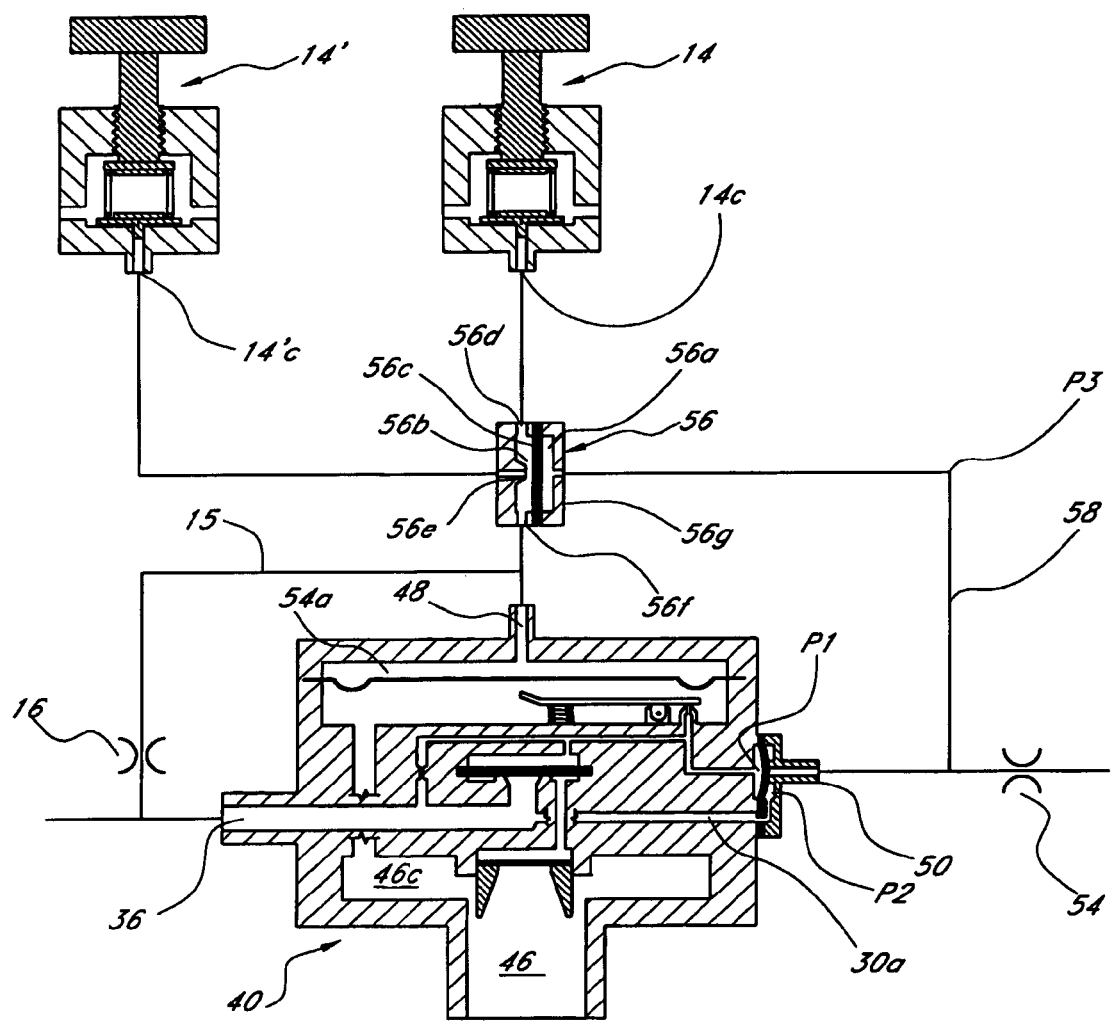
FIGS. 13 and 14 are schematic cross-sectional views of a bi-level controlled demand valve functioning with two independently adjustable pressure regulators in the exhalation and inhalation modes, respectively.
Figure 14:
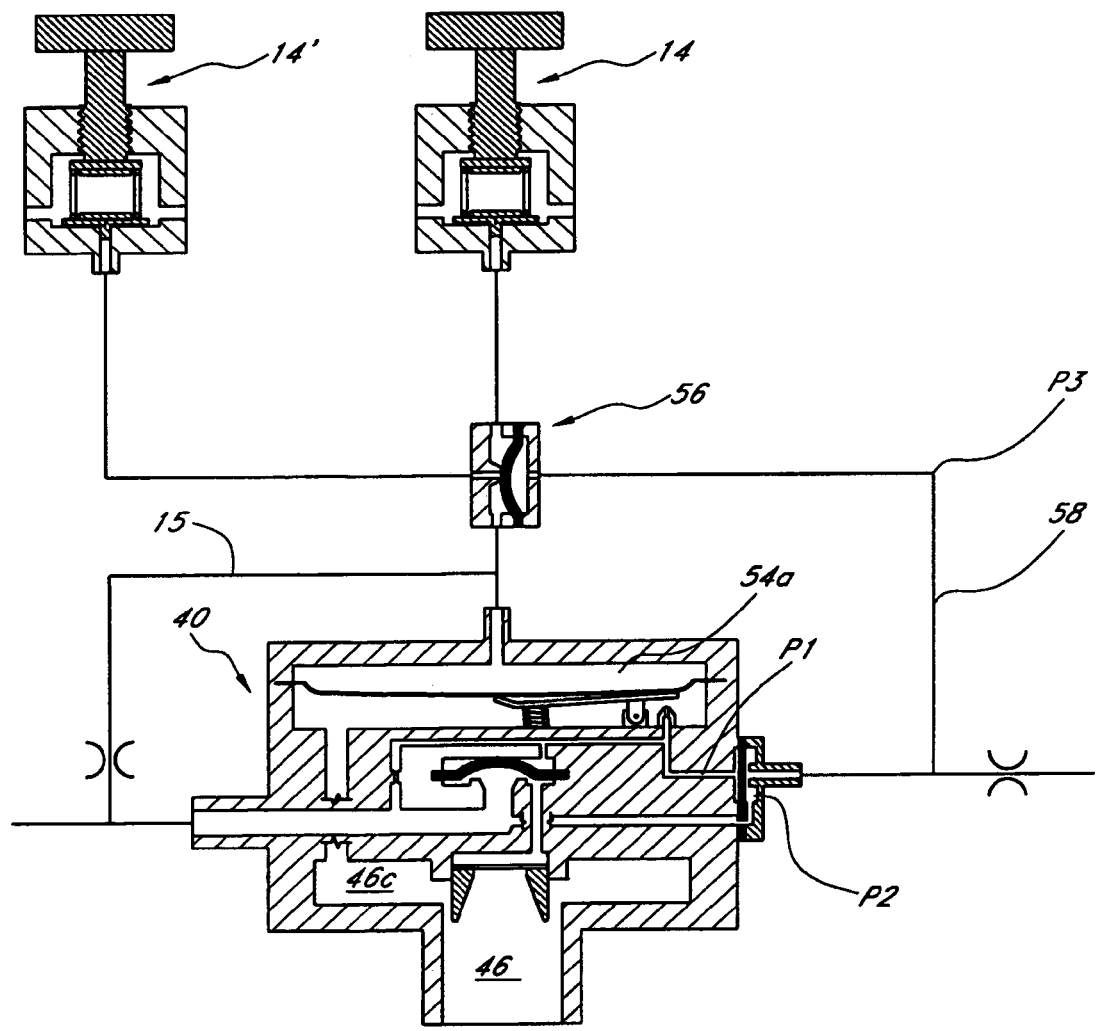

A bi-level pressure regulator is illustrated in FIGS. 13 and 14 configured in the exhalation and inhalation modes, respectively. An additional adjustable back pressure regulator 14' and an inhalation/exhalation responsive or selector valve 56 enables an operator to adjust separate reference pressures for the exhalation and inhalation phases of the breathing cycle. The valve 56 includes chambers 56a and 56b disposed on opposite sides of a diaphragm 56c. The valve has outlet ports 56d and 56e connected to the inlets 14c and 14c' of the pressure regulators 14 and 14' as shown. A first inlet port 56f is connected to line 15 and the reference chamber 54a. A second inlet 56g is connected to nebulizer outlet, via line 58.

In the exhalation mode the pressure P3 (FIG. 12) in line 60 and chamber 56a is low and the valve 56 is open connecting the line 15 and reference chamber to the inlets of both pressure regulators. As a result the reference pressure is dictated by the pressure regulator having the lowest pressure setting, i.e., valve 14'. In the inhalation mode, with the main valve open, the pressure P3 in line 60 rises to force diaphragm 56c against the seat surrounding the outlet 56e thereby connecting only the inlet of the regulator 14 to the line 15 and the reference chamber. In this mode the reference pressure is set by the regulator 14.

Where the system is equipped with two independently adjustable pressure regulators, as in FIGS. 13 and 14, the exhalation pressure experienced by the patient may be adjusted to any level equal to or below (down to atmospheric pressure) the inhalation pressure. Thus, a patient's effort required to exhale may be considerably reduced.

Figure 15:
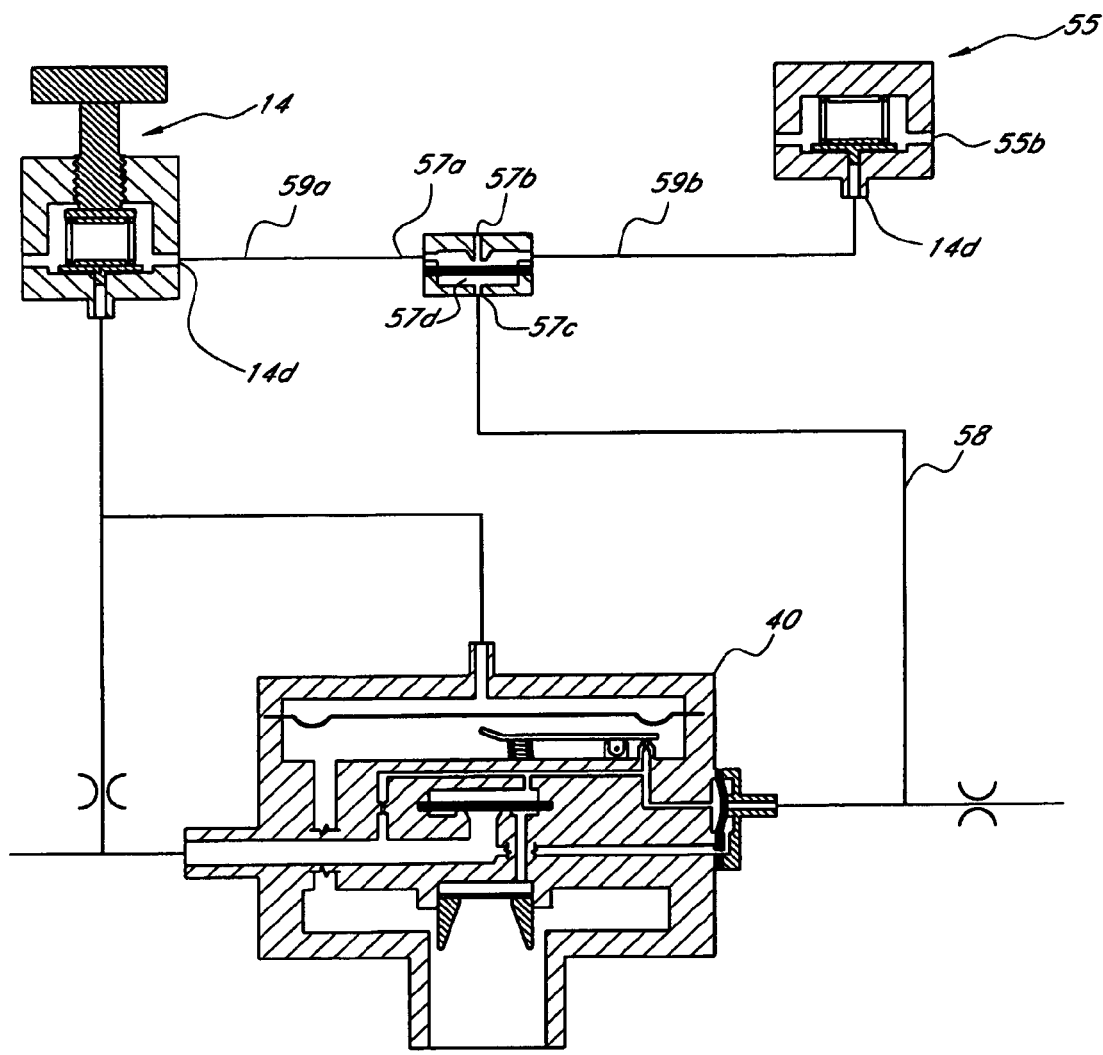
FIGS. 15 and 16 are schematic cross-sectional views of a bi-level controlled demand valve with only one field adjustable pressure regulator configured in the exhalation and inhalation modes, respectively.
Figure 16:
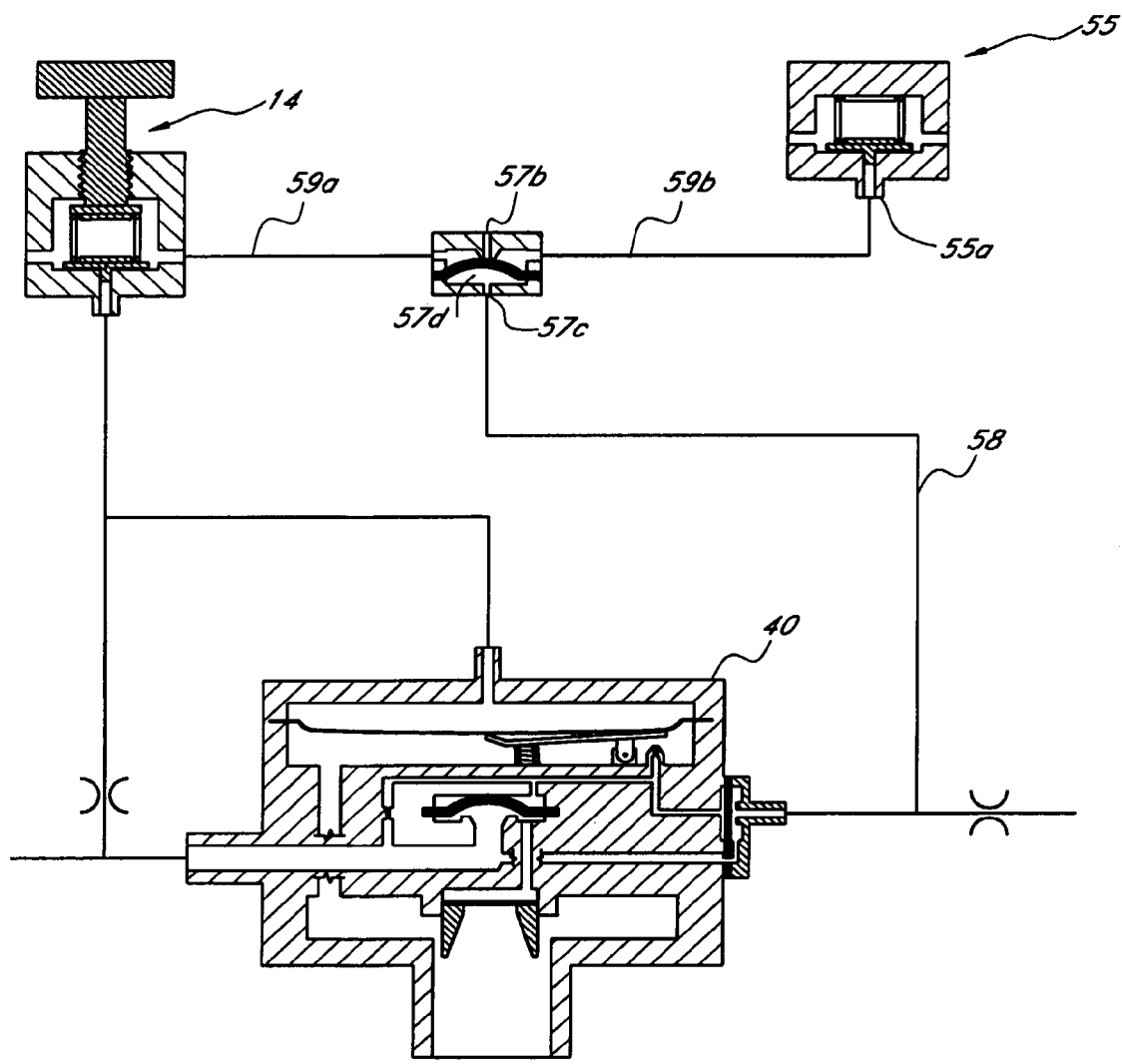

An alternative embodiment of a bi-level system is illustrated in FIGS. 15 and 16. This system functions in similar manner with one of the pressure regulators, i.e., regulator 55 being preadjusted at the factory to connect its input 55*a* to atmosphere via output 55*b* at a selected pressure, e.g., 10 cm $H_2O$. A selector diaphragm valve 57 connects the outlet 14*d* of pressure regulator 14 to atmosphere via line 59*a*, inlet port 57*a*, and outlet port 57*b* during the exhalation mode as is illustrated in FIG. 15. During the inhalation mode (FIG. 16) the rise in pressure in line 60 (P3, FIG. 12) transmitted through inlet orifice 57*c* causes diaphragm 57*d* to close outlet 57*b*, connecting the outlet of pressure regulator 14 to the inlet 55*a* of pressure regulator 55. Thus, the inhalation pressure will always be a fixed pressure (e.g., 10 cm $H_2O$)above the exhalation pressure as set by the manually adjustable pressure regulator 14.

It is to be noted that the term manually adjustable as used herein is not to be interpreted as limited to a rotatable knob arrangement. The term is to be interpreted to include any arrangement which allows the operator to readily change the reference pressure before and during a treatment.

Figure 17:
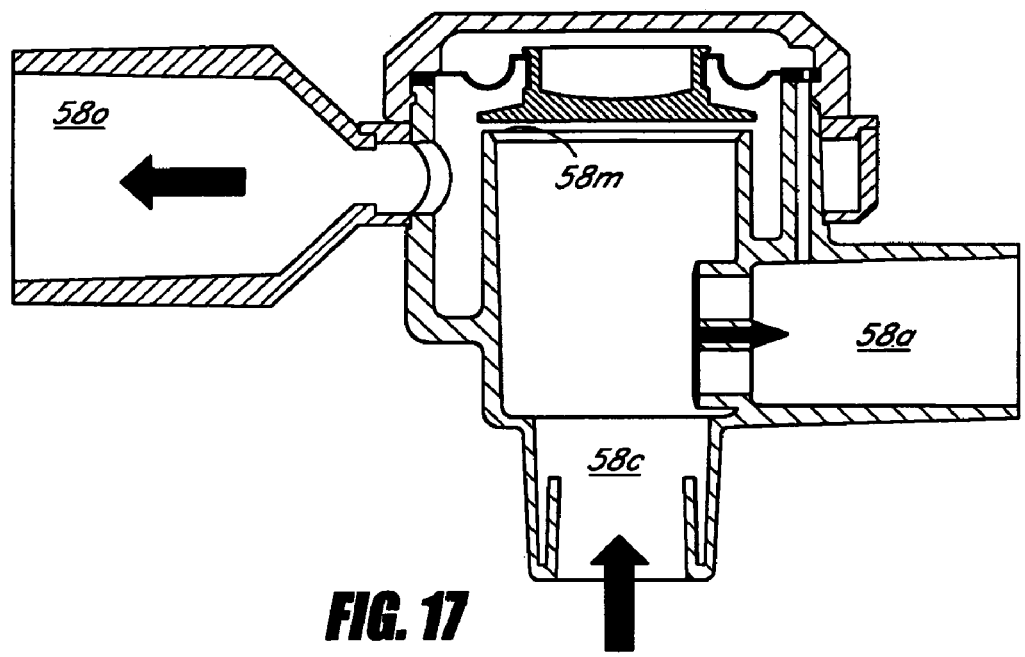
FIGS. 17 and 18 are schematic cross-sectional views of an improved face mask valve for use with the invention as configured in the exhalation and inhalation modes, respectively.
Figure 18:
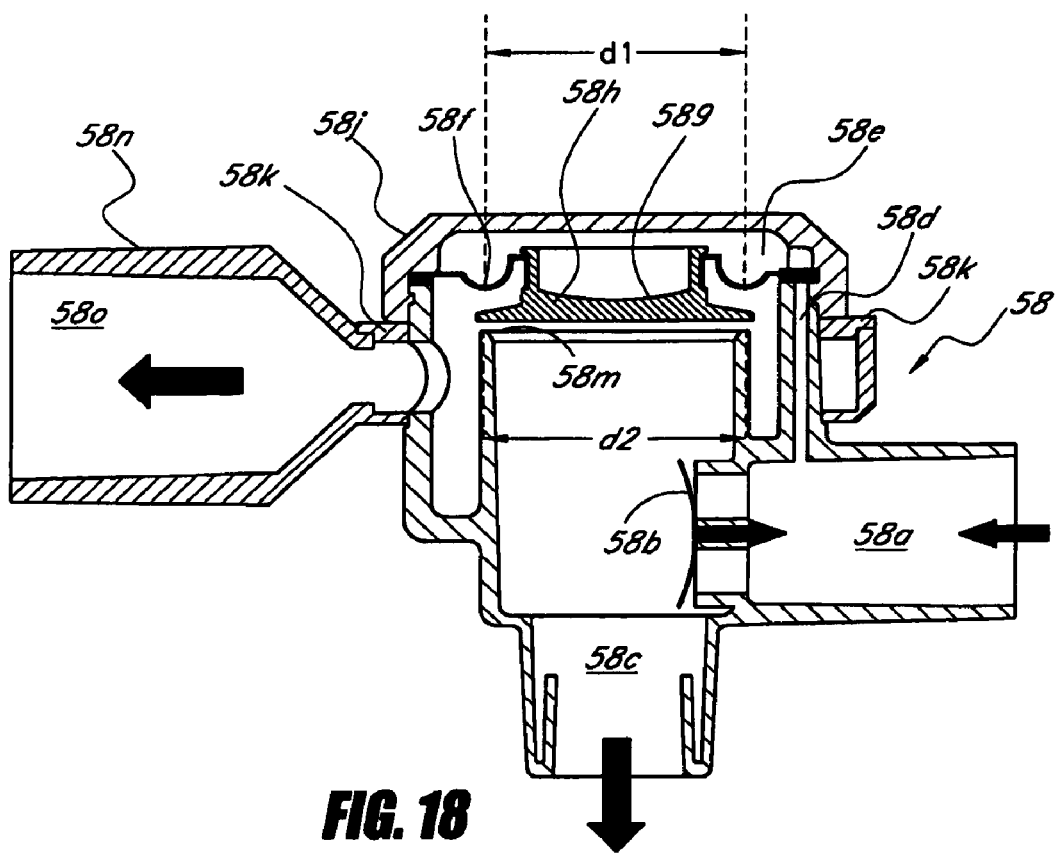
Figure 19:
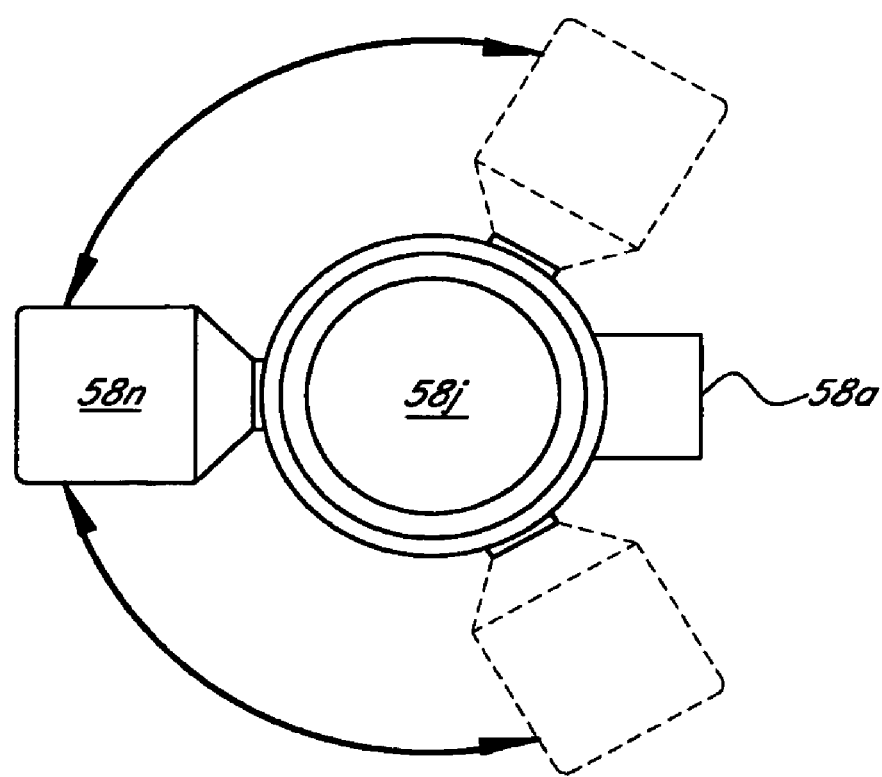
FIG. 19 is a top plan view of the face mask valve showing the angle through which the atmospheric outlet stub can swivel around the housing.

FIGS. 17 and 18 illustrate a cross-sectional schematic view of an improved patient valve arrangement 58 for use with or incorporation into a patient's face mask in accordance with this invention. The patient valve 58 comprises an inlet passage 58*a* terminating in an inhalation check valve 58*b* that acts to permit flow from the inlet 58*a* to an inlet/outlet chamber 58*c* which in turn is adapted to be placed in fluid communication with the patient's airway via a face mask etc. A passage 58*d* conducts gas ($O_2$) from the inlet to a diaphragm chamber 58*e*. This chamber is formed by the upper surface of diaphragm 58*f* secured at its periphery to the inner wall of valve housing 58*j*, the upper top central surface 58*g* of a circular valve member 58*h* and the interior of an upper section 58*i* of the generally cylindrically shaped valve housing 58*j* as illustrated. The valve member 58*h* is secured to and suspended by the radially inner portion of the diaphragm. This chamber 58*e* acts to provide pneumatic damping and pressure balance to the operation of valve member 58*h*. When the patient exhales, the pressure in the inlet/outlet chamber 58*c* rises above the pressure in the inlet 58*a*. This causes check valve 58*b* to close, allowing diaphragm 58*f* and valve member 58*h* to move upwardly lifting the valve member off of its annular seat 58*m* formed at the upper (terminal) end of the inlet/outlet chamber 56*c*. Flow is then directed through an exhaust casing 58*k* which surrounds the valve seat and thence to exhaust port 58*n* and to atmosphere via passage 58*o*. The exhaust port, formed in exhaust casing 58*l*, which is rotatable through an angle of about 300° with respect to the valve housing 58*j* allows the patient's expired air to be directed as desired.

An important design feature of the valve is the balancing of the effective areas of the diaphragm 58*f* (and upper surface 58*g* of the valve member) and the valve seat area 58*m*. The effective area of the diaphragm has a diameter d1 and the median diameter of the valve seat is d2. These two diameters are preferably about equal. This feature allows the exhalation pressure to be maintained at a level almost equal to the inhalation pressure in inlet 58*a*, regardless of the positive pressure level.

There has thus been described a novel apparatus or system for supplying breathable gas such as $O_2$ under the continuous positive airway pressure technique which is portable, rugged, simple to use and very conservative in its use of $O_2$. Various modifications and additions to the disclosed apparatus will occur to those skilled in the art without involving any departing from the spirit and scope of the invention as defined in the appended claims.

What is claimed is:

1. In a pneumatically controlled continuous positive airway pressure apparatus for supplying breathable gas from a pressurized source to an individual's breathing appliance, which appliance has an inlet for receiving the gas and an inhalation/exhalation valve for routing the gas to the individual's lungs and the exhaled air to the atmosphere, the apparatus comprising:

a demand valve assembly having a supply inlet port adapted to be fluidly connected to the pressurized source, an outlet port adapted to be fluidly connected to the appliance's inlet, a reference chamber and a control assembly responsive to a pressure differential between a reference chamber pressure and an outlet port pressure for fluidly connecting and disconnecting the inlet port to and from the outlet port; and at least one adjustable back pressure regulator fluidly connected to the pressurized source and the reference chamber for setting the pressure in the reference chamber at a selected level above atmospheric pressure, wherein the demand valve assembly includes a main valve disposed between the inlet and outlet ports, wherein the control assembly causes the main valve to open and fluidly connect the inlet port to the outlet port when the outlet port pressure falls below the pressure in the reference chamber and for causing the main valve to close to fluidly disconnect the inlet from the outlet port when outlet port pressure rises to the pressure in the reference chamber;

wherein the control assembly comprises a control valve; and
the demand valve assembly includes a pressurized nebulizer outlet and a nebulizer valve responsive to the status of the control valve for fluidly connecting and disconnecting the nebulizer outlet to the inlet port when the control valve is closed and opened, respectively.

2. In a pneumatically controlled continuous positive airway pressure apparatus for supplying breathable gas from a pressurized source to an individual's breathing appliance, which appliance has an inlet for receiving the gas and an inhalation/exhalation valve for routing the gas to the individual's lungs and the exhaled air to the atmosphere, the apparatus comprising:

a demand valve assembly having a supply inlet port adapted to be fluidly connected to the pressurized source, an outlet port adapted to be fluidly connected to the appliance's inlet, a reference chamber and a control valve assembly responsive to a pressure differential between a reference chamber pressure and an outlet port pressure for fluidly connecting and disconnecting the inlet port to and from the outlet port; and at least one adjustable back pressure regulator fluidly connected to the pressurized source and the reference chamber for setting the pressure in the reference chamber at a selected level above atmospheric pressure, wherein the demand valve assembly includes a main valve disposed between the inlet and outlet ports,
the control valve assembly comprises a control valve,
the control valve assembly causes the main valve to open and fluidly connect the inlet non to the outlet port when the outlet port pressure falls below the pressure in the reference chamber and for causing the main valve to close to fluidly disconnect the inlet from the outlet port when outlet port pressure rises to the pressure in the reference chamber, the main valve comprises a diaphragm valve with first and second actuating chambers disposed on opposite sides of the diaphragm, the area of the diaphragm exposed to the second chamber being smaller than the area of the diaphragm exposed to the first chamber whereby the main valve will remain closed when the pressure in the two actuating chambers is substantially the same and will open when the pressure in the first chamber falls below the pressure in the second chamber by a preset amount, and the nebulizer valve is a diaphragm valve with first and second chambers disposed on opposite sides of the diaphragm, the first chamber being in fluid communication with the first chamber of the main valve, the second chamber of the nebulizer valve being in fluid communication with the nebulizer outlet and with the second chamber of the main valve through a flow restrictor.

3. In a pneumatically controlled continuous positive airway pressure apparatus for supplying breathable gas from a pressurized source to an individual's breathing appliance, which appliance has an inlet for receiving the gas and an inhalation/exhalation valve for routing the gas to the individual's lungs and the exhaled air to the atmosphere, the apparatus comprising:

a demand valve assembly having a supply inlet port adapted to be fluidly connected to the pressurized source, an outlet port adapted to be fluidly connected to the appliance's inlet, a reference chamber and a control assembly responsive to a pressure differential between a reference chamber pressure and an outlet port pressure for fluidly connecting and disconnecting the inlet port to and from the outlet port; and at least one adjustable back pressure regulator fluidly connected to the pressurized source and the reference chamber for setting the pressure in the reference chamber at a selected level above atmospheric pressure, wherein the demand valve assembly includes a main valve disposed between the inlet and outlet ports, wherein the control assembly causes the main valve to open and fluidly connect the inlet port to the outlet port when the outlet port pressure falls below the pressure in the reference chamber and for causing the main valve to close to fluidly disconnect the inlet from the outlet port when outlet port pressure rises to the pressure in the reference chamber;

the main valve comprises a diaphragm valve with first and second actuating chambers disposed on opposite sides of the diaphragm, the area of the diaphragm exposed to the second chamber being smaller than the area of the diaphragm exposed to the first chamber whereby the main valve will remain closed when the pressure in the two actuating chambers is substantially the same and will open when the pressure in the first chamber falls below the pressure in the second chamber by a preset amount;

the control assembly comprises a control valve comprising a diaphragm valve with the reference chamber and a second chamber disposed on opposite sides of a pressure sensing diaphragm, the second chamber being in fluid communication with the outlet port;

both chambers of the main valve are fluidly connected to the inlet port, the fluid connection to the first chamber including a restrictor for restricting the flow rate;

the control assembly further includes a normally closed pilot valve fluidly connected to the first chamber of the main valve, the pilot valve opening to fluidly connect the first chamber of the main valve to the second chamber of the control valve in response to the movement of the sensing diaphragm as a result of the pressure in the second chamber of the control valve falling below the pressure in the reference chamber; and the pilot valve includes a spring biased member which maintains the pilot valve normally closed.

4. In a pneumatically controlled continuous positive airway pressure apparatus for supplying breathable gas from a pressurized source to an individual's breathing appliance, which appliance has an inlet for receiving the gas and an inhalation/exhalation valve for routing the gas to the individual's lungs and the exhaled air to the atmosphere, the apparatus comprising:

a demand valve assembly having a supply inlet port adapted to be fluidly connected to the pressurized source, an outlet port adapted to be fluidly connected to the appliance's inlet, a reference chamber and a control assembly responsive to a pressure differential between a reference chamber pressure and an outlet port pressure for fluidly connecting and disconnecting the inlet port to and from the outlet port; and at least one adjustable back pressure regulator fluidly connected to the pressurized source and the reference chamber for setting the pressure in the reference chamber at a selected level above atmospheric pressure, wherein the demand valve assembly includes a main valve disposed between the inlet and outlet ports, wherein the control assembly causes the main valve to open and fluidly connect the inlet port to the outlet port when the outlet port pressure falls below the pressure in the reference chamber and for causing the main valve to close to fluidly disconnect the inlet from the outlet port when outlet port pressure rises to the pressure in the reference chamber;

the main valve comprises a diaphragm valve with first and second actuating chambers disposed on opposite sides of the diaphragm, the area of the diaphragm exposed to the second chamber being smaller than the area of the diaphragm exposed to the first chamber whereby the main valve will remain closed when the pressure in the two actuating chambers is substantially the same and will open when the pressure in the first chamber falls below the pressure in the second chamber by a preset amount;

the control assembly comprises a control valve comprising a diaphragm valve with the reference chamber and a second chamber disposed on opposite sides of a pressure sensing diaphragm, the second chamber being in fluid communication with the outlet port;

both chambers of the main valve are fluidly connected to the inlet port, the fluid connection to the first chamber including a restrictor for restricting the flow rate;

further comprising a nebulizer valve, wherein the nebulizer valve is a diaphragm valve having first and second actuating chambers disposed on opposite sides of the diaphragm, the first chamber being in fluid communication with the first chamber of the main valve, the second chamber being in fluid communication with a pressurized nebulizer outlet.

5. In a pneumatically controlled continuous positive airway pressure apparatus for supplying breathable gas from a pressurized source, to an individual's breathing appliance, which appliance has an inlet for receiving the gas and an inhalation/exhalation valve for routing the gas to the individual's lungs and the exhaled air to the atmosphere, the apparatus comprising:

a demand valve assembly having a supply inlet port adapted to be fluidly connected to the pressurized source, an outlet port adapted to be fluidly connected to the appliance's inlet, a reference chamber and a control assembly responsive to a pressure differential between a reference chamber pressure and an outlet port pressure for fluidly connecting and disconnecting the inlet port to and from the outlet port; and at least one adjustable back pressure regulator fluidly connected to the pressurized source and the reference chamber for setting the pressure in the reference chamber at a selected level above atmospheric pressure, wherein the demand valve assembly includes a main valve disposed between the inlet and outlet ports, wherein the control assembly causes the main valve to open and fluidly connect the inlet port to the outlet port when the outlet port pressure falls below the pressure in the reference chamber and for causing the main valve to close to fluidly disconnect the inlet from the outlet port when outlet port pressure rises to the pressure in the reference chamber; and at least one adjustable pressure regulator includes a line with a flow restrictor fluidly connected between the pressurized source and the reference chamber and a first adjustable poppet valve fluidly connected between said line upstream from the flow restrictor and atmosphere.

6. In a pneumatically controlled continuous positive airway pressure apparatus for supplying breathable gas from a pressurized source to an individual's breathing appliance, which appliance has an inlet for receiving the gas and an inhalation/exhalation valve for routing the gas to the individual's lungs and the exhaled air to the atmosphere, the apparatus comprising:

a demand valve assembly having a supply inlet port adapted to be fluidly connected to the pressurized source, an outlet part adapted to be fluidly connected to the appliance's inlet, a reference chamber and a control assembly responsive to a pressure differential between a reference chamber pressure and an outlet port pressure for fluidly connecting and disconnecting the inlet port to and from the outlet port; and at least one adjustable back pressure regulator fluidly connected to the pressurized source and the reference chamber for setting the pressure in the reference chamber at a selected level above atmospheric pressure, wherein the demand valve assembly includes a main valve disposed between the inlet and outlet ports, wherein the control assembly causes the main valve to open and fluidly connect the inlet port to the outlet port when the outlet port pressure falls below the pressure in the reference chamber and for causing the main valve to close to fluidly disconnect the inlet from the outlet port when outlet port pressure rises to the pressure in the reference chamber;

the control assembly comprises a control valve; and said at least one pressure regulator comprises two pressure regulators, at least one which is manually adjustable and a inhalation/exhalation selector, the two pressure regulators in conjunction with the selector being arranged to set the pressure in the reference chamber at one level during the inhalation phase and at a different level during the exhalation phase.

7. The apparatus of claim 6, wherein the reference chamber is fluidly connected to the pressurized source through a restrictor and wherein each pressure regulator includes a poppet valve, each poppet valve having an inlet and an outlet, the outlets being in fluid communication with the atmosphere, the inlet of one of the poppet valves being in constant fluid communication with the reference chamber upstream from the restrictor, and further including a selector valve for placing the inlet of the other poppet valve in fluid communication with the reference chamber, upstream of the restrictor, in response to the closure of the main valve.

8. The apparatus of claim 7, wherein both pressure regulators are manually adjustable.

9. The apparatus of claim 7, wherein the selector valve is a diaphragm valve.

10. The apparatus of claim 9, wherein the selector valve includes first and second chambers disposed on opposite sides of the diaphragm with the first chamber being in fluid communication with a nebulizer outlet and the second chamber being in fluid communication with the reference chamber.

11. The apparatus of claim 6, wherein the other pressure regulator is not manually adjustable by an operator in the field and functions to set the pressure in the reference chamber at a set pressure above the exhalation reference pressure during the inhalation phase.

12. The apparatus of claim 11, wherein each of the pressure regulators includes a poppet valve and the selector comprises a diaphragm valve.

13. In a pneumatically controlled CPAP apparatus for supplying breathable $O_2$ from a pressurized source to an individual's breathing appliance, which appliance has a patient valve with an inlet for receiving the $O_2$ and an inhalation/exhalation valve for routing the $O_2$ to the individual's lungs and the exhaled air to the atmosphere, the apparatus comprising:

a demand valve, having a supply inlet port adapted to be connected to the pressurized source, an outlet port adapted to be connected to the appliance's inlet and a valve assembly responsive to a reference pressure and an appliance inlet pressure for connecting the inlet port to the outlet port when the appliance inlet pressure falls below the reference pressure and for disconnecting the inlet port from the outlet port when the appliance inlet pressure rises to the reference pressure; and at least one adjustable back pressure regulator coupled to the demand valve for allowing an operator to set the reference pressure at a selected level above atmospheric and change that level during the treatment of a patient, wherein said at least one pressure regulator comprises two pressure regulators, one of which is manually adjustable by the operator and an inhalation/exhalation selector, the two pressure regulators in conjunction with the selector being arranged to set the reference pressure at one level during an inhalation phase and at a lower level during an exhalation phase.

14. In a pneumatically controlled CPAP apparatus for supplying breathable $O_2$ from a pressurized source to an individual's breathing appliance, which appliance has a patient valve with an inlet for receiving the $O_2$ and an inhalation/exhalation valve for routing the $O_2$ to the individual's lungs and the exhaled air to the atmosphere, the apparatus comprising:

a demand valve having a supply inlet port adapted to be connected to the pressurized source, an outlet port adapted to be connected to the appliance's inlet and a valve assembly responsive to a reference pressure and an appliance inlet pressure for connecting the inlet port to the outlet port when the appliance inlet pressure falls below the reference pressure and for disconnecting the inlet port from the outlet port when the appliance inlet pressure rises to the reference pressure; and at least one adjustable back pressure regulator coupled to the demand valve for allowing an operator to set the reference pressure at a selected level above atmospheric and change that level during the treatment of a patient, wherein the demand valve includes a pressurized nebulizer outlet and a valve responsive to the flow of $O_2$ between the inlet and outlet port for connecting and disconnecting the nebulizer outlet to the inlet port when the inlet port is connected to and disconnected from the outlet port, respectively.

15. In a pneumatically controlled CPAP apparatus for supplying breathable $O_2$ from a pressurized source to an individual's breathing appliance, which appliance has a patient valve with an inlet for receiving the $O_2$ and an inhalation/exhalation valve for routing the $O_2$ to the individual's lungs and the exhaled air to the atmosphere, the apparatus comprising:

a demand valve having a supply inlet port adapted to be connected to the pressurized source, an outlet port adapted to be connected to the appliance's inlet and a valve assembly responsive to a reference pressure and an appliance inlet pressure for connecting the inlet port to the outlet port when the appliance inlet pressure falls below the reference pressure and for disconnecting the inlet port from the outlet port when the appliance inlet pressure rises to the reference pressure; and at least one adjustable back pressure regulator coupled to the demand valve for allowing an operator to set the reference pressure at a selected level above atmospheric and change that level during the treatment of a patient, further including a pressure gauge connected to the demand valve to inform an operator of the selected reference pressure.

16. The apparatus of claim 15, wherein said at least one operator adjustable pressure regulator is connected to the pressurized source as well as to the demand valve and wherein the demand valve includes a reference chamber for receiving the reference pressure and wherein the valve assembly is arranged to compare the appliance inlet pressure with the pressure in the reference chamber.

17. The apparatus of claim 16, wherein said at least one operator adjustable pressure regulator includes a line with a flow restrictor connected between the pressurized source and the reference chamber and a first adjustable poppet valve connected between said line upstream from the flow restrictor and atmosphere.

* * * * *

UNITED STATES PATENT AND TRADEMARK OFFICE
CERTIFICATE OF CORRECTION

PATENT NO. : 7,066,175 B2
APPLICATION NO. : 10/020544
DATED : June 27, 2006
INVENTOR(S) : Robert M. Hamilton and Anthony J. Gambone It is certified that error appears in the above-identified patent and that said Letters Patent is hereby corrected as shown below:

At Column 4, line 27, delete "25 29" and insert -- 29 --, therefor.

At Column 4, line 40, delete "41 42" and insert -- 42 --, therefor.

At Column 4, line 63, delete "15a 15" and insert -- 15 --, therefor.

At Column 8, line 66, delete "non" and insert -- port --, therefor.

At Column 11, line 6, delete "source," and insert -- source --, therefor.

At Column 11, line 48, delete "part" and insert -- port --, therefor.

At Column 12, line 47 (approx.), delete "valve," and insert -- valve --, therefor.

Signed and Sealed this

Twenty-fourth Day of July, 2007

JON W. DUDAS
*Director of the United States Patent and Trademark Office*